(12) United States Patent
Yeomans

(10) Patent No.: US 10,900,012 B2
(45) Date of Patent: Jan. 26, 2021

(54) PROBE

(71) Applicant: Aber Instruments Limited, Powys (GB)

(72) Inventor: Paul Yeomans, Ynyslas (GB)

(73) Assignee: Aber Instruments Limited

( * ) Notice: Subject to any disclaimer, the term of this patent is extended or adjusted under 35 U.S.C. 154(b) by 540 days.

(21) Appl. No.: 15/494,472

(22) Filed: Apr. 22, 2017

(65) Prior Publication Data

US 2017/0355948 A1 Dec. 14, 2017

(30) Foreign Application Priority Data

May 5, 2016 (GB) .................................. 1607890.9

(51) Int. Cl.
*C12M 1/34* (2006.01)
*G01N 33/487* (2006.01)
(Continued)

(52) U.S. Cl.
CPC ....... *C12M 41/46* (2013.01); *B29C 45/14065* (2013.01); *B29C 45/14336* (2013.01);
(Continued)

(58) Field of Classification Search
CPC ...... C12M 41/46; C12M 23/26; C12M 23/46; C12M 41/00; C12M 27/16; C12M 41/36;
(Continued)

(56) References Cited

U.S. PATENT DOCUMENTS 4,353,488 A * 10/1982 Schneiter ............... B67D 3/045
222/501
4,803,365 A * 2/1989 Krause ................... G01N 21/64
250/432 R (Continued)

FOREIGN PATENT DOCUMENTS

WO WO 2010/010313 A2 1/2010
WO WO 2015/085214 6/2015
WO WO 2016/124500 8/2016

OTHER PUBLICATIONS

European Search Report in EPO application 17166377.6-1501, dated Oct. 9, 2017.

(Continued)

*Primary Examiner* — William H. Beisner
*Assistant Examiner* — Danielle B Henkel
(74) *Attorney, Agent, or Firm* — Muskin and Farmer LLC

(57) ABSTRACT

A probe assembly and a method of manufacturing a probe assembly. In one aspect there is a method of manufacturing a probe assembly comprising providing an electrode carrier carrying a plurality of electrodes, the electrode carrier comprising a top wherein the plurality of electrodes are exposed relative to the top and a bottom having a plurality of electrical contacts in electrical communication with the plurality of electrodes respectively; moulding a body around the electrode carrier to retain the electrode carrier whilst leaving the plurality of electrodes exposed. The invention also extends to a biomass monitoring system comprising a flexible enclosure including a probe assembly and support (Continued)

arrangement for receipt of the probe assembly in an engaged configuration.

10 Claims, 4 Drawing Sheets

(51) Int. Cl.
| | |
|---|---|
| *B29C 45/14* | (2006.01) |
| *C12M 1/00* | (2006.01) |
| *C12M 3/00* | (2006.01) |
| *C12M 1/02* | (2006.01) |
| *G01N 33/483* | (2006.01) |
| *C12M 3/06* | (2006.01) |
| *B29L 31/34* | (2006.01) |

(52) U.S. Cl.
CPC ............ *C12M 23/26* (2013.01); *C12M 23/46* (2013.01); *C12M 27/00* (2013.01); *C12M 41/00* (2013.01); *G01N 33/4836* (2013.01); *G01N 33/48735* (2013.01); *B29L 2031/3481* (2013.01); *C12M 27/16* (2013.01); *C12M 41/36* (2013.01)

(58) Field of Classification Search
CPC .............. C12M 27/00; B29C 45/14065; B29C 45/14336; G01N 33/4836; G01N 33/48735; B29L 2031/3481
See application file for complete search history.

(56) References Cited

U.S. PATENT DOCUMENTS

| | | | | |
|---|---|---|---|---|
| 5,385,477 | A * | 1/1995 | Vaynkof | ............ G01R 1/07357 |
| | | | | 439/591 |
| 8,550,439 | B2 * | 10/2013 | Terentiev | ................ B01F 13/00 |
| | | | | 261/121.1 |
| 2006/0011474 | A1 * | 1/2006 | Schulein | ............ G01N 27/3276 |
| | | | | 204/403.01 |
| 2006/0219564 | A1 | 10/2006 | Feng | |
| 2009/0100911 | A1 | 4/2009 | Kawanishi | |
| 2009/0147617 | A1 | 6/2009 | Baumfalk | |
| 2011/0006796 | A1 | 1/2011 | Kister | |
| 2011/0187388 | A1 | 8/2011 | Ossart | |

OTHER PUBLICATIONS

Office Action/search report in priority application GB1607890.9, dated Sep. 19, 2016.
Office Action/search report in priority application GB1607890.9, dated Nov. 14, 2016.

* cited by examiner

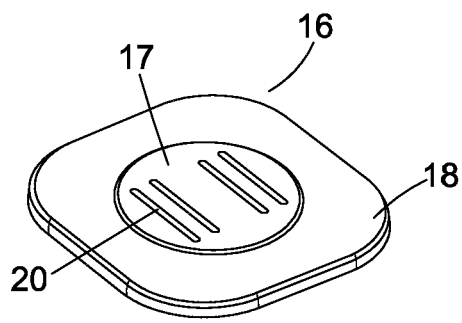
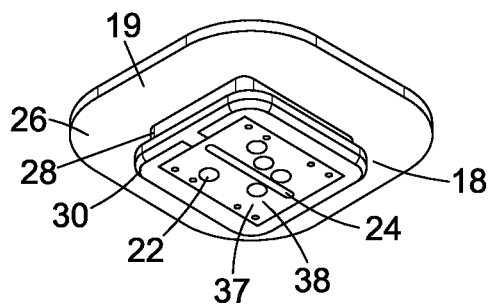
Fig. 1a   Fig. 1b
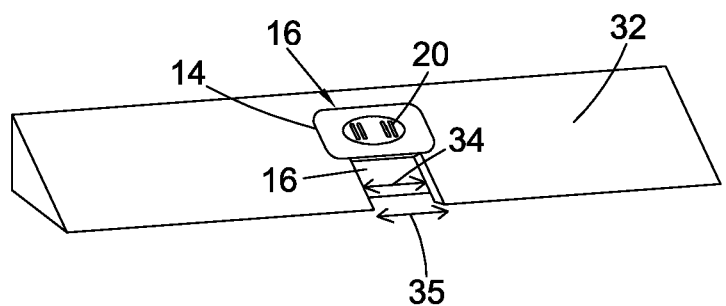
Fig. 2
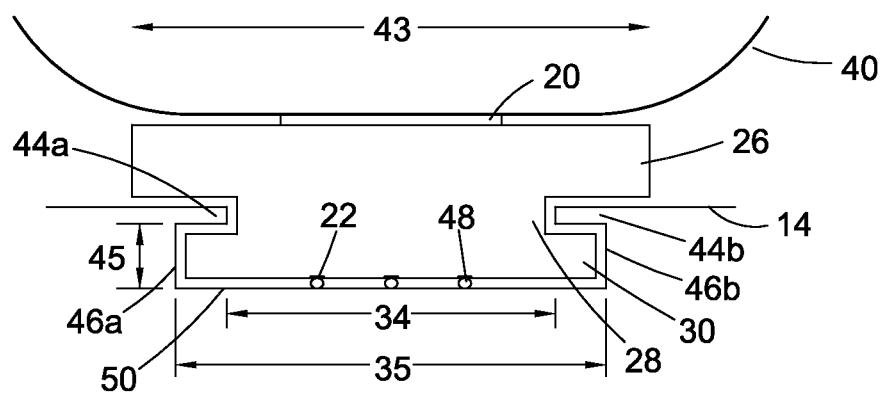
Fig. 3

PROBE

CROSS REFERENCE TO RELATED APPLICATIONS

This application claims priority under 35 U.S.C. § 119 to GB1607890.9, filed in Great Britain on May 5, 2016, which is incorporated by reference herein in its entirety.

BACKGROUND OF THE INVENTION

Field of the Invention

This invention relates generally to a probe assembly, and more particularly to a method of manufacturing a probe assembly. The invention is particularly suited, but not limited to, use in probes for biomass monitoring applications.

Description of the Related Art

Commercial-scale biomass cultivation requires the constant monitoring of biomass production. Electrical properties of biomass can be measured by special designed probes. The modern trend for disposable bioreactors created recently a need for single-use probe systems. Single-use probes are secured to single-use flexible bags that contain the biomass, and the probe electrodes create and measure the electric field in the culture and provide data about the process. The increasing demand for large volumes of single-use probes requires a method of mass production for probes that will allow fast ramp up and increased production yield. The existing method of manufacturing probes is manual, slow and unable to cover current demand as probes are assembled one by one by workers resulting in increased rates of defects, production variability and low production yield.

Existing probes designs present additional challenges in positioning them correctly in a monitoring system which while in use is typically arranged to rock the flexible bag in order to agitate the biomass. A probe and a monitoring system have to be aligned for engagement and secured. This is difficult to achieve due to the inherent flexibility of the bag and the difficulty in holding and engaging the probe.

Furthermore, the rocking motion of the bag in combination with existing probe design can lead to loosening of electrical interactions between opposing sides of the probe resulting in additional noise in data collection.

It is desirable to provide a fast to manufacture and reliable probe assembly.

Such an improved solution has now been devised.

SUMMARY OF THE INVENTION

It is an aspect of the present invention to provide a method of manufacturing a probe assembly comprising providing an electrode carrier carrying a plurality of electrodes, the electrode carrier comprising a top wherein the plurality of electrodes are exposed relative to the top and a bottom having a plurality of electrical contacts in electrical communication with the plurality of electrodes respectively; and moulding a body around the electrode carrier to retain the electrode carrier whilst leaving the plurality of electrodes exposed.

Such a method provides a significantly improved method of manufacturing a probe assembly.

The plurality of electrodes are preferably each formed of an elongate conductive element projecting from the electrode carrier, wherein a separation gap is provided between at least a portion of the electrode and the top of the electrode carrier wherein the moulding step introduces material of the body into the separation gap. This is beneficial as this ensures integrity of the probe whilst in use avoiding potential leak paths for the biomass that is typically present in a flexible bioreactor into which the probe will be mounted.

Opposing ends of the plurality of electrodes are preferably located into corresponding electrode receiving formations in the electrode carrier. This step is carried out prior to the moulding step.

The ends are beneficially fixed into the corresponding receiving formations. The ends may be soldered into the corresponding receiving formations.

The electrode carrier beneficially comprises one or more sides provided between the top and the bottom, and wherein the body is moulded around some or all of the one or more sides. It is beneficial that the electrode carrier comprises four sides and preferably the body is moulded around all four sides. The sides may be encapsulated. It will be appreciated, however, that the body is preferably not moulded over the bottom. The electrode carrier however is effectively retained by the body.

The bottom of the electrode carrier preferably comprises a holding formation and is held by the holding formation during moulding of the body, and wherein the method preferably further comprises a step of removing the holding formation after moulding. The holding formation may comprise an indent, opening or other formation in the bottom of the electrode carrier. This is held during moulding of the body. The holding formation is preferably removed after moulding. This may be achieved, for example, by filling.

The body preferably comprises a primary flange having an abutment surface for engaging with a flexible enclosure. This abutment surface is adhered to a flexible bioreactor enclosure for use. It is preferable that the primary flange is integrally moulded with the body.

According to a further aspect of the present invention there is a biomass monitoring system comprising a flexible enclosure defining a cavity, the flexible enclosure having an opening therein, the system further comprising a probe assembly comprising a top carrying a plurality of electrodes and a primary flange secured to the flexible enclosure to occlude the opening such that the plurality of electrodes are in communication with the cavity, the probe assembly further comprising a secondary flange spaced apart from the primary flange and defining a channel therebetween and a plurality of electrical contacts in electrical communication with the plurality of electrodes provided on a bottom of the probe assembly externally of the cavity; the system further comprising a support arrangement having a guide channel for receipt of the secondary flange in slideable engagement, the support arrangement further comprising electrical contact elements arranged to electrically communicate with the plurality of electrical contacts of the probe assembly in an engaged configuration.

The primary and the secondary flanges are beneficially substantially parallel. It is beneficial that the slideable engagement is in an axis substantially perpendicular to an axis between the top and the bottom. The support arrangement preferably comprises a support surface for supporting the enclosure and the slot preferably projects substantially parallel to the plane of the support surface. As such, the flexible enclosure including the probe beneficially sit on the support arrangement.

In the engaged configuration the primary flange is beneficially positioned externally of the guide channel. Accordingly, the secondary flange is retained in the guide channel whereas the primary flange is external of the guide channel.

The guide channel beneficially comprises a width defined by a first and second side wall and a top and bottom, the top having an opening therein extending between opposing shoulders, wherein the opposing shoulders extend into the channel defined between the primary and secondary flange portions of the probe in the engaged configuration.

The guide channel is beneficially open substantially perpendicular to the contact surface of the electrical contacts of the probe. The guide channel beneficially extends generally parallel to the active portion of the electrodes.

The support arrangement is beneficially configured to retain the probe in the engaged configuration. This is important as during operation of the biomass monitoring system the support arrangement beneficially moves in a rocking motion to agitate the content of the flexible enclosure. As such, it is beneficial to retain the probe in the engaged configuration. This is preferably achieved through the electrical contact elements of the support arrangement being deflectably mounted and being arranged to bias the secondary flange into communication with the opposing shoulders. Accordingly, the electrical contact elements are beneficially in the form of spring loaded pins.

The guide channel beneficially comprises a mouth, and the shoulders taper inwardly in a direction into the guide channel away from the mouth. This is beneficial in order to improve accessibility of the probe and the support arrangement and enables guiding of the probe onto the support arrangement.

The secondary flange beneficially comprises a first and second flange portion, wherein the first flange portion and primary flange define a first channel and the second flange portion and primary flange define a second channel. Accordingly, in the engaged configuration two sides of the probe are retained by these support arrangements.

The support arrangement is beneficially arranged to cause agitation of the flexible enclosure and probe in operation. The support arrangement beneficially is configured to rock to cause agitation.

The probe assembly beneficially comprises an electrode carrier and a body, wherein the body comprises the primary and secondary flanges, and wherein the body is formed around the electrode carrier to retain the electrode carrier whilst leaving the plurality of electrodes exposed.

The electrode carrier is preferably seated in the body, the electrode carrier comprising the plurality of electrical contacts, and a separation gap is defined between a portion of the plurality of electrodes and the electrode carrier, wherein the body extends into the separation gap.

According to a further aspect of the present invention there is a probe assembly comprising a top carrying a plurality of electrodes, a primary flange for securing to a flexible enclosure and a secondary flange spaced apart from the primary flange defining a channel therebetween, the probe assembly further comprising a plurality of electrical contacts in electrical communication with the plurality of electrodes provided on a bottom of the probe assembly, the secondary flange arranged to slideably engage with a support arrangement.

These together with other aspects and advantages which will be subsequently apparent, reside in the details of construction and operation as more fully hereinafter described and claimed, reference being had to the accompanying drawings forming a part hereof, wherein like numerals refer to like parts throughout.

BRIEF DESCRIPTION OF THE DRAWINGS

Further features and advantages of the present invention, as well as the structure and operation of various embodiments of the present invention, will become apparent and more readily appreciated from the following description of the preferred embodiments, taken in conjunction with the accompanying drawings of which:

FIGS. 1a and 1b are perspective schematic views of a probe according to an exemplary embodiment of the present invention;

FIG. 2 is a schematic view of a biomass monitoring system including engaged probe according to an exemplary embodiment of the present invention;

FIG. 3 is a schematic cross sectional view of a probe located in the biomass monitoring system according to an exemplary embodiment of the present invention;

DESCRIPTION OF THE PREFERRED EMBODIMENTS

Figure 4C:
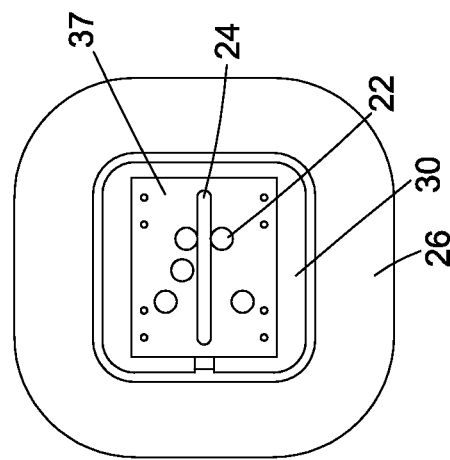
FIGS. 4a, 4b and 4c are top, side and bottom schematic views of a probe according to an exemplary embodiment of the present invention.

Reference will now be made in detail to the presently preferred embodiments of the invention, examples of which are illustrated in the accompanying drawings, wherein like reference numerals refer to like elements throughout.

FIGS. 1a and 1b illustrates probe 16 comprising electrodes 20, a probe body 18 and electrode carrier 37. The probe 16 has a top 17 and bottom 19. The probe body 18 is formed around electrode carrier 37. Probe body 18 comprises primary flange 16, neck 28, and secondary flange 30. The electrode carrier 37 comprises electrode body 38, electrical contacts 22 for electrically communicating with the electrodes 20 and holding formation 24. The plane of primary flange 16 and the plane of secondary flange 30 are substantially parallel. The middle part connecting the primary flange 26 and secondary flange 30 forms a neck 28.

FIG. 2 is an exemplary schematic representation of the use of the probe 16 positioned in a support arrangement 32 having a support surface 14. The support arrangement 32 is configured to cause agitation of the biomass retained inside a flexible enclosure not shown in FIG. 2 for clarity purposes. A guide channel 36 is formed to receive the secondary flange 30 and primary flange 26 is arranged to sit externally on the top of support arrangement 34. The top surface of the primary flange 26 is adhered to a flexible bag (removed for clarity purposes). Guide channel 36 comprises a slot having a width 34 open outwardly and width 35 to receive and guide probe 14.

Referring to FIG. 2 in combination with FIG. 3, the flexible enclosure 40 is adhered to the top surface of the primary flange 36. FIG. 3 represents a side view of the guide channel 36, into which the probe 16 has been positioned. In this position the lower surface of the primary flange 26 abuts the support surface 14 that surrounds the guide channel 36. Shoulders 44a, 44b of the support arrangement 32 project into the guide channel 36 beneath which the secondary flange 30 is received. Accordingly, the width of the outwardly facing opening 34 through which the probe projects when engaged is less than the width 35 of the guide channel 36 in which the secondary flange 30 is received. The direction of insertion of the probe 16 into the guide channel 36 is along an axis substantially perpendicular to an axis between the top and bottom of probe 16.

Electrical contact elements 48 are configured to electrically communicate with the probe electrical contacts 22. Electrical contact elements 48 can be spring loaded pins. In an engaged position electrical contact elements 48 exert pressure on the secondary flange 30 of the probe to the retain probe in an engaged position. Electrical contact elements 48 can be deflectable and are arranged to bias the secondary flange 30 into communication with the opposing shoulders 44a, 44b. Guide channel 36 is substantially perpendicular to the direction or deflection of the contact elements 48.

Figure 4B:
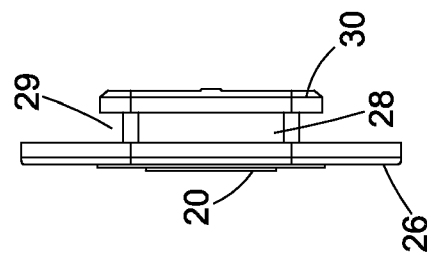
Figure 4A:
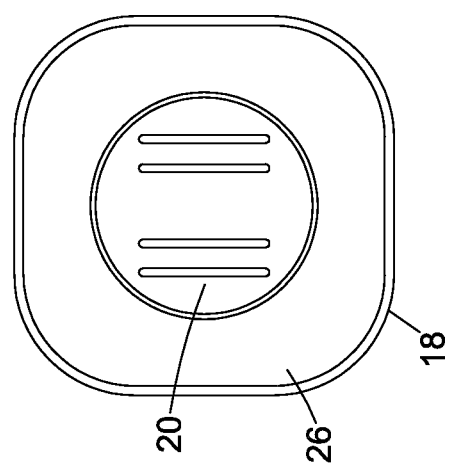

FIGS. 4a, 4b, 4c are top, side and bottom schematic views of a probe 16. An injection moulding process may be used to form the probe body 18 around the electrode carrier 37. The elongated electrodes 20 are left exposed in order that contact with the biomass is enabled when the probe is in operation. The bottom part of the electrode carrier 37 is also exposed to be allow the electrical contacts 22 to electrically communicate with the spring loaded contact elements 48 of the support arrangement 34. As shown in FIG. 4(b) the neck 28 along with the primary flange 26 and secondary flange 30 define an engagement channel 29 for receipt of the shoulders 44a, 44b.

Figures 5A, 5B:
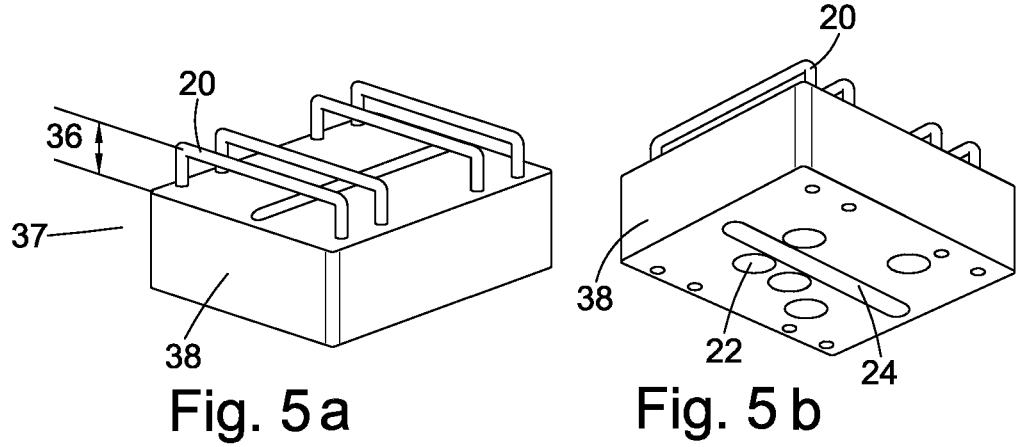
FIGS. 5a and 5b are perspective top and bottom schematic views of the electrode carrier forming part of a probe according to an exemplary embodiment of the present invention.

FIGS. 5a and 5b present an electrode carrier 37 comprising an electrode carrier body 38, having a plurality (four in the exemplary embodiment) of elongated electrodes 20 positioned above the top of the electrode carrier body 38 and on the bottom are electrical contacts 22 and holding formation 24. The holding formation 24 is grasped by the moulding machine. A separation gap 36 is present between at least a portion of the electrodes 20 and the electrode carrier body 38 top surface. During the moulding step, material of the probe is introduced to the separation gap 36. Holding formation 24 is used to secure the electrical carrier 37 inside the mould during the (injection) moulding process. Electrical contacts 22 are located in the bottom of the electrode carrier 37 and are in electrical contact with the elongated electrodes 20 as further explained with respect to FIGS. 3 and 4.

Figure 6:
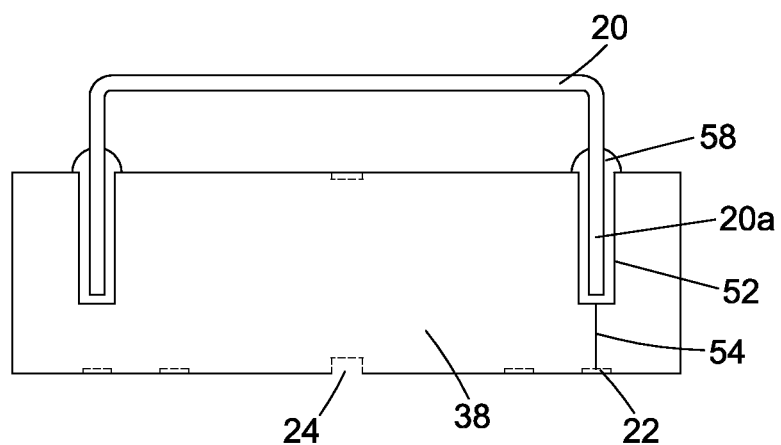
FIG. 6 is a cross section of the electrode carrier of FIG. 5.

FIG. 6 is a cross sectional representation of the electrode carrier 37. Electrode ends 20a extend in a perpendicular direction to elongated portions of electrodes 20. The electrode ends 20a are positioned in corresponding electrode receiving formations 52 that extend into the electrode carrier body 38. Receiving formations 52 are electrically connected to electrical contacts 22 positioned at the bottom of electrical carrier 37 by electrical connection lines 54. Electrode ends 20a are inserted in a perpendicular direction relative to the top surface of the electrode carrier body 38. The elongated top portions of the electrodes 20 are positioned in parallel to electrode carrier 37 top surface. Electrodes 20 are secured by soldering 58 in receiving formations 52 prior to a moulding step. When electrodes 20 are secured, the separation gap 36 is formed between electrodes 20 and the electric carrier body 38. The separation gap 36 is filled with material to form part of the probe body 18 during the moulding step.

Figure 7:
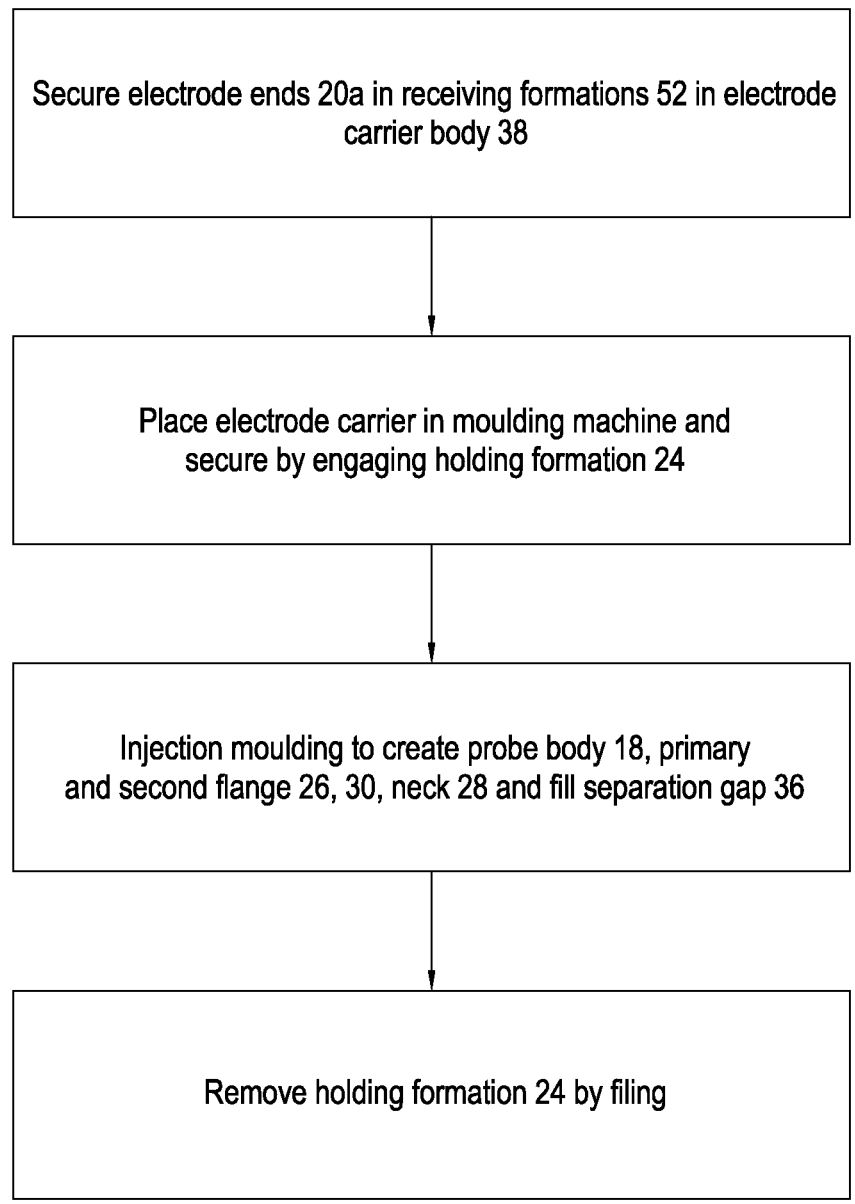
FIG. 7 is a block diagram of an exemplary manufacturing process of the present invention.

FIG. 7 presents an overview of the manufacturing process for production of a probe according to an exemplary embodiment. Firstly electrodes ends 20a are secured or soldered in receiving formations 52 in the electrode carrier body 38. The electrode carrier 37 is then placed inside a moulding machine and held in place by holding formation 24. The probe body 18 comprising primary flange 26, secondary flange 30, neck 28, and the separation gap 36 is filled by moulding. The holding formation 24 can then be removed post moulding, for example by filling with resin.

It should be noted that the above-mentioned embodiments illustrate rather than limit the invention, and that those skilled in the art will be capable of designing many alternative embodiments without departing from the scope of the invention as defined by the appended claims. In the claims, any reference signs placed in parentheses shall not be construed as limiting the claims. The singular reference of an element does not exclude the plural reference of such elements and vice-versa. In a device claim enumerating several means, several of these means may be embodied by one and the same item of hardware. The mere fact that certain measures are recited in mutually different dependent claims does not indicate that a combination of these measures cannot be used to advantage.

The many features and advantages of the invention are apparent from the detailed specification and, thus, it is intended by the appended claims to cover all such features and advantages of the invention that fall within the true spirit and scope of the invention. Further, since numerous modifications and changes will readily occur to those skilled in the art, it is not desired to limit the invention to the exact construction and operation illustrated and described, and accordingly all suitable modifications and equivalents may be resorted to, falling within the scope of the invention.

What is claimed is:

1. A biomass monitoring system comprising:
a flexible enclosure defining a cavity, the flexible enclosure having an opening therein;
the system further comprising a probe assembly comprising a top carrying a plurality of electrodes and primary flange and a bottom comprising a plurality of electrical contacts in electrical communication with the plurality of electrodes external of the cavity; the primary flange secured to an outer face of the flexible enclosure to occlude the opening such that the plurality of electrodes are in communication with the cavity;
the probe assembly further comprising a secondary flange spaced apart from the primary flange and defining a channel therebetween;
the system further comprising a support arrangement having a guide channel for receipt of the secondary flange in slideable engagement; and
the support arrangement further comprising electrical contact elements arranged to electrically communicate with the plurality of electrical contacts of the probe assembly in an engaged configuration, wherein the secondary flange is slideable from a disengaged configuration where the plurality of electrical contacts of the probe assembly are misaligned with the electrical contact elements of the support arrangement to the engaged configuration, and wherein the secondary flange is further slidable from the engaged to the disengaged configuration.

2. A biomass monitoring system according to claim 1 wherein the support arrangement comprises a support surface for supporting the flexible enclosure, and the guide channel is open substantially parallel to a plane of the support surface.

3. A biomass monitoring system according to claim 1 wherein in the engaged configuration the primary flange is positioned externally of the guide channel.

4. A biomass monitoring system according to claim 1 wherein the guide channel has a width defined by a first and second side wall and a top and bottom, the top having an opening therein extending between opposing shoulders, wherein the opposing shoulders extend into the channel defined between the primary and secondary flange portions of the probe assembly in the engaged configuration.

5. A biomass monitoring system according to claim 4 wherein the electrical contact elements are deflectably mounted and are arranged to bias the secondary flange into communication with the opposing shoulders.

6. A biomass monitoring system according to claim 4 wherein the channel comprises a mouth, and the shoulders taper inwardly in a direction into the channel away from the mouth.

7. A biomass monitoring system according to claim 1 wherein the secondary flange comprises a first and second flange portion, wherein the first flange portion and primary flange define a first channel, and the second flange portion and primary flange define a second channel.

8. A biomass monitoring system according to claim 1 wherein the support arrangement is arranged to cause agitation of the flexible enclosure and probe in operation.

9. A biomass monitoring system according to claim 8 wherein the probe assembly comprises an electrode carrier and a body, wherein the body comprises the primary and secondary flanges, and wherein the body is formed around the electrode carrier to retain the electrode carrier whilst leaving the plurality of electrodes exposed.

10. A biomass monitoring system according to claim 9 wherein the electrode carrier is seated in the body, the electrode carrier comprising the plurality of electrical contacts, and a separation gap is defined between a portion of the plurality of electrodes and the electrode carrier, wherein the body extends into the separation gap.

* * * * *